United States Patent
Chang et al.

(10) Patent No.: US 11,903,671 B2
(45) Date of Patent: Feb. 20, 2024

(54) FREQUENCY MODULATED CONTINUOUS WAVE RADAR SYSTEM AND IDENTITY AND INFORMATION DETECTION METHOD THEREOF

(71) Applicant: Wistron Corporation, New Taipei (TW)

(72) Inventors: Yao-Tsung Chang, New Taipei (TW); Yin-Yu Chen, New Taipei (TW); Chuan-Yen Kao, New Taipei (TW)

(73) Assignee: Wistron Corporation, New Taipei (TW)

( * ) Notice: Subject to any disclaimer, the term of this patent is extended or adjusted under 35 U.S.C. 154(b) by 159 days.

(21) Appl. No.: 17/353,797

(22) Filed: Jun. 21, 2021

(65) Prior Publication Data

US 2022/0299628 A1    Sep. 22, 2022

(30) Foreign Application Priority Data

Mar. 17, 2021   (TW) ................................ 110109487
Mar. 17, 2021   (TW) ................................ 110109639

(51) Int. Cl.
*G01S 7/35*     (2006.01)
*G01S 7/41*     (2006.01)
(Continued)

(52) U.S. Cl.
CPC .......... *A61B 5/0015* (2013.01); *A61B 5/0004* (2013.01); *A61B 5/7257* (2013.01);
(Continued)

(58) Field of Classification Search
CPC ........ G01S 7/356; G01S 7/412; G01S 13/756; G01S 13/825
See application file for complete search history.

(56) References Cited

U.S. PATENT DOCUMENTS 4,292,637 A    9/1981   Johnson
7,567,200 B1   7/2009   Osterweil
(Continued)

FOREIGN PATENT DOCUMENTS

CN    108700645 A    10/2018
CN    111932826 A    11/2020
(Continued)

OTHER PUBLICATIONS

Rajab WO 2018206934 A1 (Year: 2018).*
(Continued)

*Primary Examiner* — Timothy A Brainard
*Assistant Examiner* — Helena H Seraydaryan
(74) *Attorney, Agent, or Firm* — Winston Hsu

(57) ABSTRACT

A frequency modulated continuous wave radar system includes at least one identity tag, respectively disposed next to at least one test subject; and a frequency modulated continuous wave radar identity recognition device, including an identity recognition control module, for controlling a test identity tag of the at least one identity tag to be turned on to generate a specific tag reflection signal corresponding to an identity frequency in response to a chirp signal; and a frequency modulated continuous wave radar, for transmitting the chirp signal and receiving at least one reflection signal of the at least one test subject and the specific tag reflection signal in response to the chirp signal, to calculate and determine that the specific tag reflection signal and a specific reflection signal of the at least one reflection signal are corresponding to an adjacent position information. The specific reflection signal is corresponding to test subject information.

16 Claims, 8 Drawing Sheets

(51) Int. Cl.
 *G01S 13/75* (2006.01)
 *A61B 5/00* (2006.01)
 *G01S 13/58* (2006.01)
 *G01S 13/82* (2006.01)

(52) U.S. Cl.
 CPC .............. *G01S 7/356* (2021.05); *G01S 7/412* (2013.01); *G01S 13/584* (2013.01); *G01S 13/756* (2013.01); *G01S 13/825* (2013.01)

(56) References Cited

U.S. PATENT DOCUMENTS

| | | | |
|---|---|---|---|
| 7,884,753 B2 * | 2/2011 | Peczalski | H04Q 9/00 340/505 |
| 2008/0074307 A1 | 3/2008 | Boric-Lubecke | |
| 2010/0231410 A1 | 9/2010 | Seisenberger | |
| 2012/0022348 A1 | 1/2012 | Droitcour | |
| 2012/0268308 A1 | 10/2012 | Tuttle | |
| 2014/0184447 A1 * | 7/2014 | Zhou | G01S 13/84 342/127 |
| 2016/0363648 A1 * | 12/2016 | Mindell | G01S 7/003 |
| 2018/0301945 A1 * | 10/2018 | Ishida | H02J 50/20 |
| 2019/0265345 A1 * | 8/2019 | Jungmaier | G01S 13/04 |
| 2020/0165934 A1 * | 5/2020 | Schleif | G01M 5/0033 |
| 2020/0200892 A1 * | 6/2020 | Rajab | G01S 13/82 |
| 2020/0237252 A1 | 7/2020 | Lane | |
| 2020/0389770 A1 | 12/2020 | Marschalkowski | |

FOREIGN PATENT DOCUMENTS

| | | |
|---|---|---|
| JP | 2019-92726 A | 6/2019 |
| JP | 2020-118598 A | 8/2020 |
| WO | 2020/128150 A1 | 6/2020 |

OTHER PUBLICATIONS

D1, JP 3675741 (Year: 2005).*
Sandeep Rao, "Introduction to mmwave Sensing: FMCW Radars", Apr. 28, 2017.
Strobel, "A Millimeter-Wave Low-Power Active Backscatter Tag for FMCW Radar Systems", May 2013.
Lazaro, "Backscatter Transponder Based on Frequency Selective Surface for FMCW Radar Applications", 2014.

* cited by examiner

FREQUENCY MODULATED CONTINUOUS WAVE RADAR SYSTEM AND IDENTITY AND INFORMATION DETECTION METHOD THEREOF

BACKGROUND OF THE INVENTION

1. Field of the Invention

The present invention relates to a frequency modulated continuous wave radar system and an identity and information detection method thereof, and more particularly, to a frequency modulated continuous wave radar system and an identity and information detection method thereof which are able to turn on a tag reflector of a specific identity tag to have an identity frequency so as to obtain test subject information adjacent to the specific identity tag intended to be measured.

2. Description of the Prior Art

In recent years, vital sign information detection technology (such as infrared body temperature measurement, blood glucose concentration detection, blood oxygen concentration detection) has flourished. The vital sign information detection technology also includes vital sign information detection for non-individual use. For example, a non-contact heartbeat and breathing frequency detection device may transmit radio frequency (RF) signals to a test subject and receive the corresponding reflection signal. This reflection signal may be modulated by the movement of the body of the test subject (such as the body displacement caused by the heartbeat and the breathing). After the reflection signal is received, demodulated, filtered and amplified, the internal algorithm of a processor can calculate the heartbeat and breathing frequency of the test subject.

Although the conventional continuous wave (CW) radar technology can remotely measure the vital sign information (such as the heartbeat and the breathing) of the test subject, it is difficult to correctly detect the vital sign information (such as the heartbeat and the breathing) of a designated test subject from a group of test subjects. Moreover, reflection signals may be interfered seriously by neighboring people or objects, thereby increasing the difficulty of measurement.

Accordingly, there is still room for improvement when it comes to vital sign information detection technology.

SUMMARY OF THE INVENTION

In order to solve aforementioned problem(s), the present invention provides a frequency modulated continuous wave radar system and an identity and information detection method thereof to turn on a tag reflector of a specific identity tag to have an identity frequency so as to obtain test subject information adjacent to the specific identity tag intended to be measured.

The present invention discloses a frequency modulated continuous wave radar system. The frequency modulated continuous wave radar system includes at least one identity tag, respectively disposed next to at least one test subject; and a frequency modulated continuous wave radar identity recognition device, The frequency modulated continuous wave radar identity recognition device includes an identity recognition control module, for transmitting a control signal to control a test identity tag of the at least one identity tag to be turned on and to make the test identity tag generate a specific tag reflection signal corresponding to an identity frequency in response to a chirp signal; and a frequency modulated continuous wave radar, for transmitting the chirp signal and receiving at least one reflection signal of the at least one test subject and the specific tag reflection signal in response to the chirp signal, to calculate and determine that the specific tag reflection signal and a specific reflection signal of the at least one reflection signal correspond to an adjacent position information. The specific reflection signal corresponds to a test subject information.

The present invention discloses an identity and information detection method for a frequency modulated continuous wave radar system. The identity and information detection method includes respectively disposing at least one identity tag next to at least one test subject; transmitting a control signal to control a test identity tag of the at least one identity tag to be turned on; by a frequency modulated continuous wave radar, transmitting a chirp signal; by the test identity tag, generating a specific tag reflection signal corresponding to an identity frequency in response to the chirp signal; and by the frequency modulated continuous wave radar, receiving at least one reflection signal of the at least one test subject and the specific tag reflection signal in response to the chirp signal to calculate and determine that the specific tag reflection signal and a specific reflection signal of the at least one reflection signal correspond to an adjacent position information. The specific reflection signal corresponds to a test subject information.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
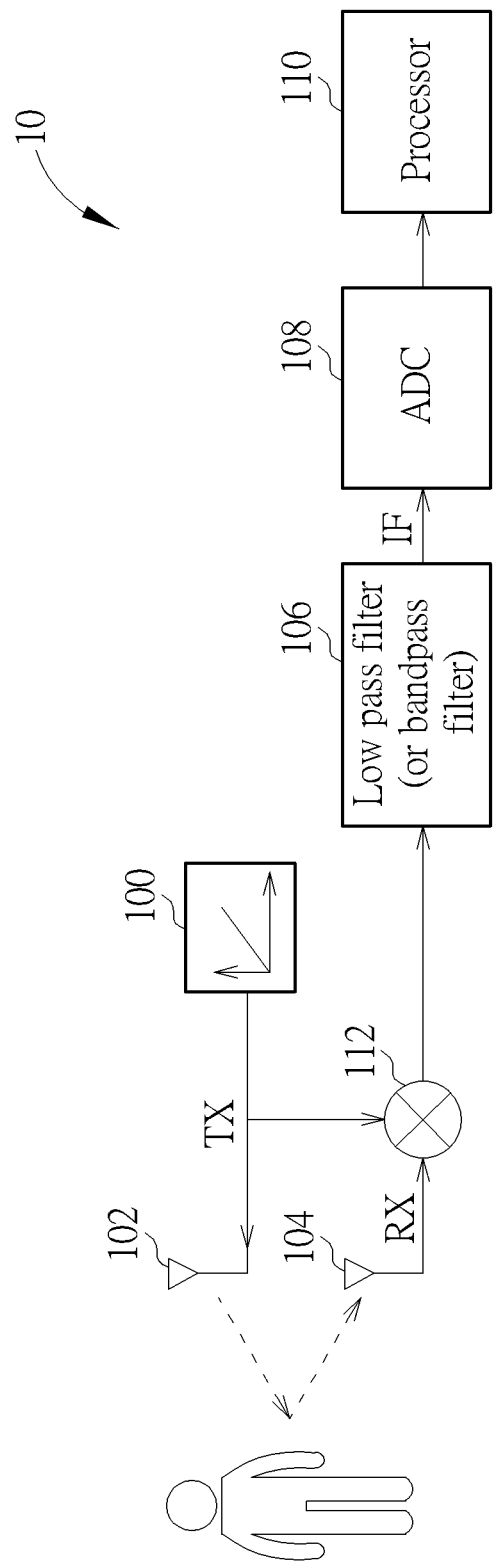
FIG. 1 is a schematic diagram of a frequency modulated continuous wave radar according to an embodiment of the present invention.

Please refer to FIG. 1. FIG. 1 is a schematic diagram of a frequency modulated continuous wave radar 10 according to an embodiment of the present invention. The difference between the frequency modulated continuous wave radar 10 and a continuous wave radar is that the continuous wave radar emits a continuous signal of fixed/stable frequency, while the frequency modulated continuous wave radar 10 emits a frequency modulated signal. In short, the frequency modulated continuous wave radar 10 includes a chirp synthesizer 100, which is configured to generate a chirp signal TX (or a linear frequency modulated signal). After the chirp signal TX is produced by the chirp synthesizer 100, the chirp signal TX flows through a transmitting circuit and is emitted from the transmitting antenna 102. The chirp signal TX may hit/bounce off an object (such as a test subject or a testee) to form a reflection signal RX. A receiving antenna 104 receives the reflection signal RX. A mixer 112 then couples the reflection signal RX received by the receiving antenna 104 with the current chirp signal TX and outputs a coupled output signal. The coupled output signal passes through a filter 106 (which is a low pass filter or a bandpass filter) to filter out high frequency signal(s)/component(s) (such as the chirp signal TX and the reflection signal RX) and generates/outputs an intermediate frequency signal IF. The intermediate frequency signal IF is converted into a digital signal by an analog-to-digital converter (ADC) 108, and then processed by a processor 110 to derive distance information, direction information and/or vital sign information.

Figure 2A:
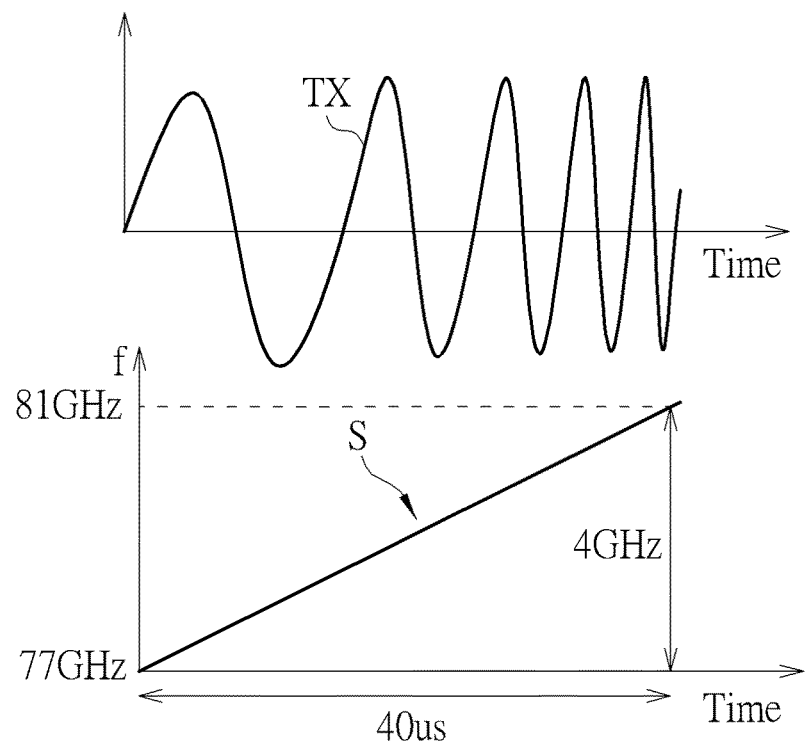
FIG. 2A is a schematic diagram of a chirp signal versus time according to an embodiment of the present invention.
Figure 2B:
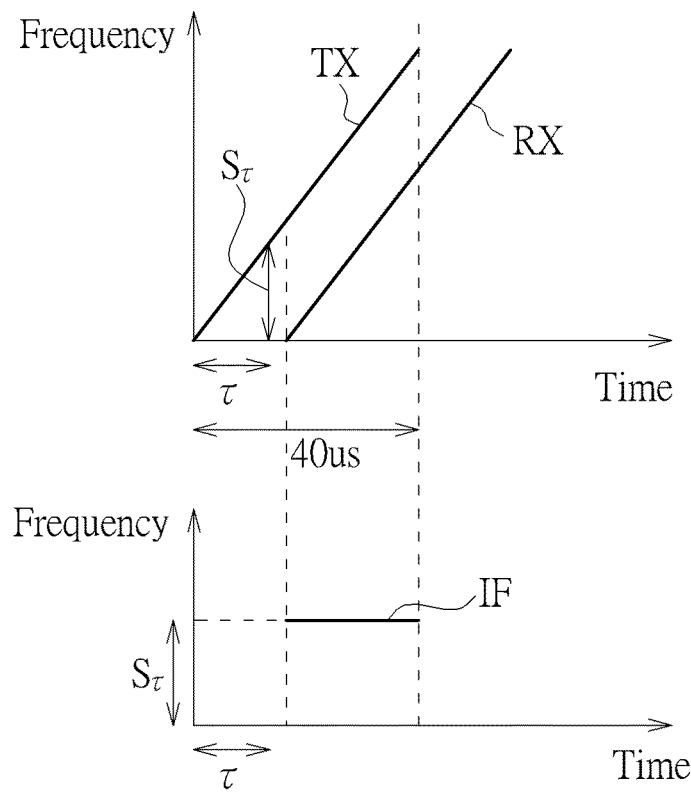
FIG. 2B is a schematic diagram of the chirp signal, a reflection signal, and an intermediate frequency signal according to an embodiment of the present invention.

Please refer to FIG. 2A and FIG. 2B. FIG. 2A is a schematic diagram of the chirp signal TX versus time according to an embodiment of the present invention. FIG. 2B is a schematic diagram of the chirp signal TX, the reflection signal RX, and the intermediate frequency signal IF according to an embodiment of the present invention. Specifically, as shown at lower part of FIG. 2A, the frequency of the chirp signal TX increases linearly over time along a modulation slope S, and hence as shown at upper part of FIG. 2A, the period of the chirp signal TX gradually narrows/decreases in the time domain. As shown at the upper part of FIG. 2B, a period of time τ after the chirp signal TX is emitted, the reflection signal RX is received/detected. Therefore, the intermediate frequency signal IF of a frequency Sτ may be obtained as shown at the lower part of FIG. 2B. The relationship may be expressed as follows:

$$TX = A_T \sin(w_1 t + \Phi_1)$$

$$RX = A_R \sin(w_2 t + \Phi_2)$$

$$IF = A_B \sin((w_1 - w_2)t + (\Phi_1 - \Phi_2)) = A_B \sin(2\pi f_0 t + \Phi_0)$$

$$f_0 = f_1 - f_2 = S\tau = 2Sd/C$$

$$\Phi_0 = (2\pi * 2d)/\lambda = 4\pi d/\lambda$$

$$\tau = 2d/C$$

where d is the distance between the test subject and frequency modulated continuous wave radar 10, and C is the signal propagation speed (speed of light). The other symbols/notations of amplitude, angular velocity, phase, frequency, and wavelength are well-known in the art, and are not detailed redundantly. From the above equations, the information of the frequency $f_0$ of the intermediate frequency signal IF implies/involves the distance d corresponding to the test subject, and the phase $\Phi_0$ of the intermediate frequency signal IF implies/involves the vital sign information (such as breathing, heartbeat, and so on) of the test subject (because the displacement of a human body caused by breathing and/or heartbeat is about 1-2 millimeter(s), which is only within a period/cycle for a millimeter wave wavelength of 12.5 mm and does not affect the frequency). Consequently, the processor 110 may obtain/have knowledge of the distance, the direction, the breathing, the heartbeat of the test subject by means of calculation/algorithm.

Figure 3:
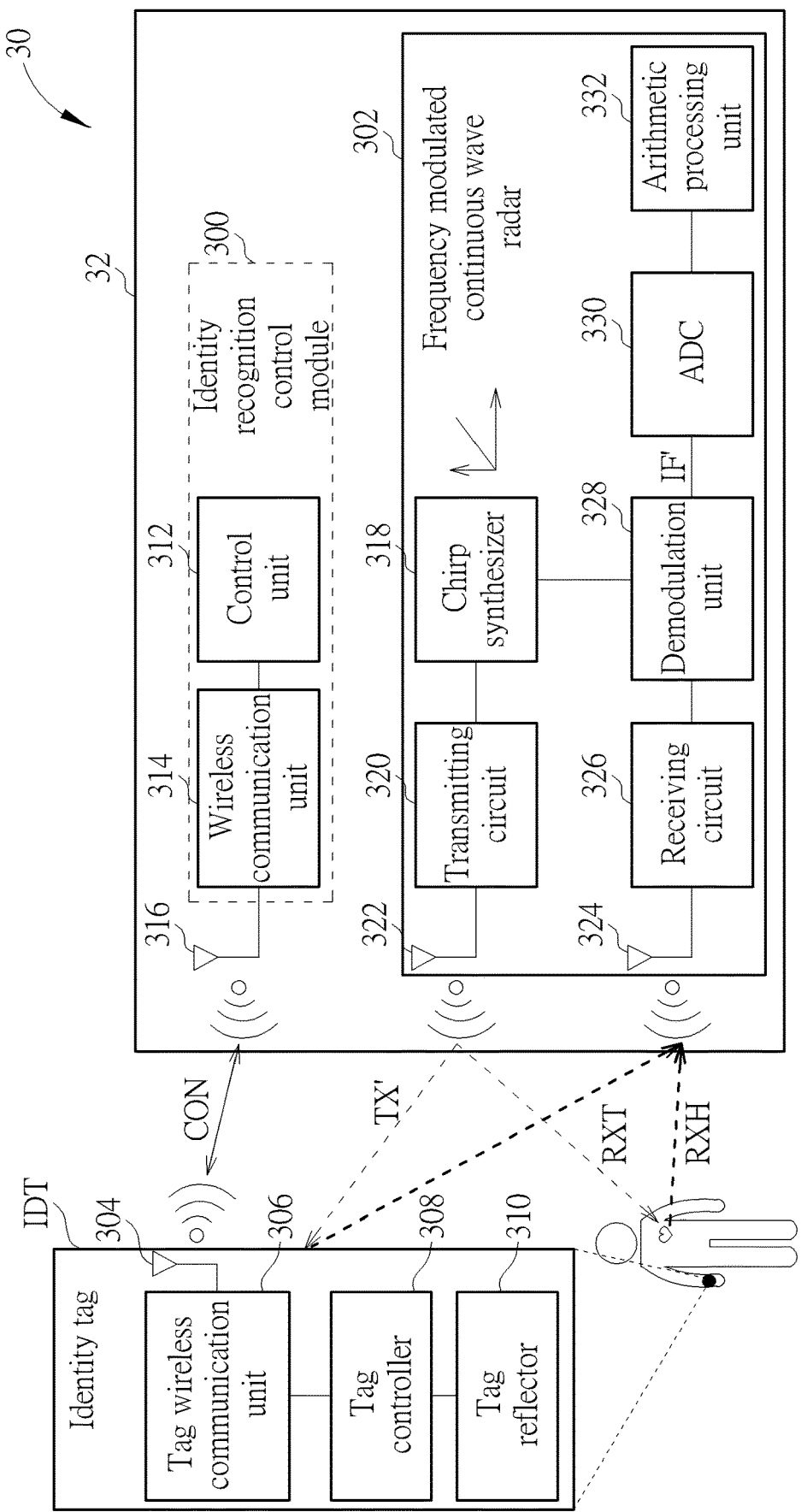
FIG. 3 is a schematic diagram of a frequency modulated continuous wave radar system according to an embodiment of the present invention.

Moreover, please refer to FIG. 3. FIG. 3 is a schematic diagram of a frequency modulated continuous wave radar system 30 according to an embodiment of the present invention. The frequency modulated continuous wave radar system 30 includes an identity tag IDT and a frequency modulated continuous wave radar recognition device 32. The frequency modulated continuous wave radar recognition device 32 includes an identity recognition control module 300 and a frequency modulated continuous wave radar 302. The identity tag IDT includes a tag antenna 304, a tag wireless communication unit/circuit 306, a tag controller 308, and a tag reflector 310. The identity recognition control module 300 includes a control unit/circuit 312, a wireless communication unit/circuit 314 and a control antenna 316. The frequency modulated continuous wave radar 302 includes a chirp synthesizer 318, a transmitting circuit 320, a transmitting antenna 322, a receiving antenna 324, a receiving circuit 326, a demodulation unit/circuit 328, an analog-to-digital converter 330 and an arithmetic processing unit/circuit 332.

Briefly, the operating principle of the frequency modulated continuous wave radar 302 is similar to that of the frequency modulated continuous wave radar 10 to obtain/measure the distance, the direction, the breathing, the heartbeat of the test subject. The main difference between the frequency modulated continuous wave radar system 30 and the frequency modulated continuous wave radar 10 is as follows: In the frequency modulated continuous wave radar system 30, the identity tag IDT, which may be turned on or off, is disposed adjacent to the test subject. (When the identity tag IDT is turned on, the tag reflector 310, by means of vibration in a specific way and so on, makes a tag reflection signal RXT have a phase change corresponding to an identity frequency.) Then, the identity recognition control module 300, through wireless communication, sends a control signal CON to control/force the identity tag IDT to be turned on. After the frequency modulated continuous wave radar 302 sends a chirp signal TX', the frequency modulated continuous wave radar 302 may receive a reflection signal RXH of the test subject and a tag reflection signal RXT of the identity tag IDT. The frequency modulated continuous wave radar 302 processes the reflection signal RXH and the (tag) reflection signal RXT to obtain/have knowledge of the distance, the direction, and/or the vital sign information (the breathing, or the heartbeat) of the test subject as well as the identity frequency, the distance, and/or the direction of the identity tag IDT. In this case, the identity tag being turned off (or having not been turned on) does not reflect/provide the tag reflection signal with identity information (such as the identity frequency). As a result, the frequency modulated continuous wave radar 302 can calculate and refer the vital sign information of the test subject to the identity tag IDT at the same distance and in the same direction, and know the measured vital sign information (the breathing, or the heartbeat) belongs to vital sign information of which test subject. In this way, the present invention may activate/turn on the tag reflector of a specific identity tag to have an identity frequency so as to obtain the vital sign information (or physiological information) of the test subject adjacent to the specific identity tag and intended to be measured.

Figure 4:
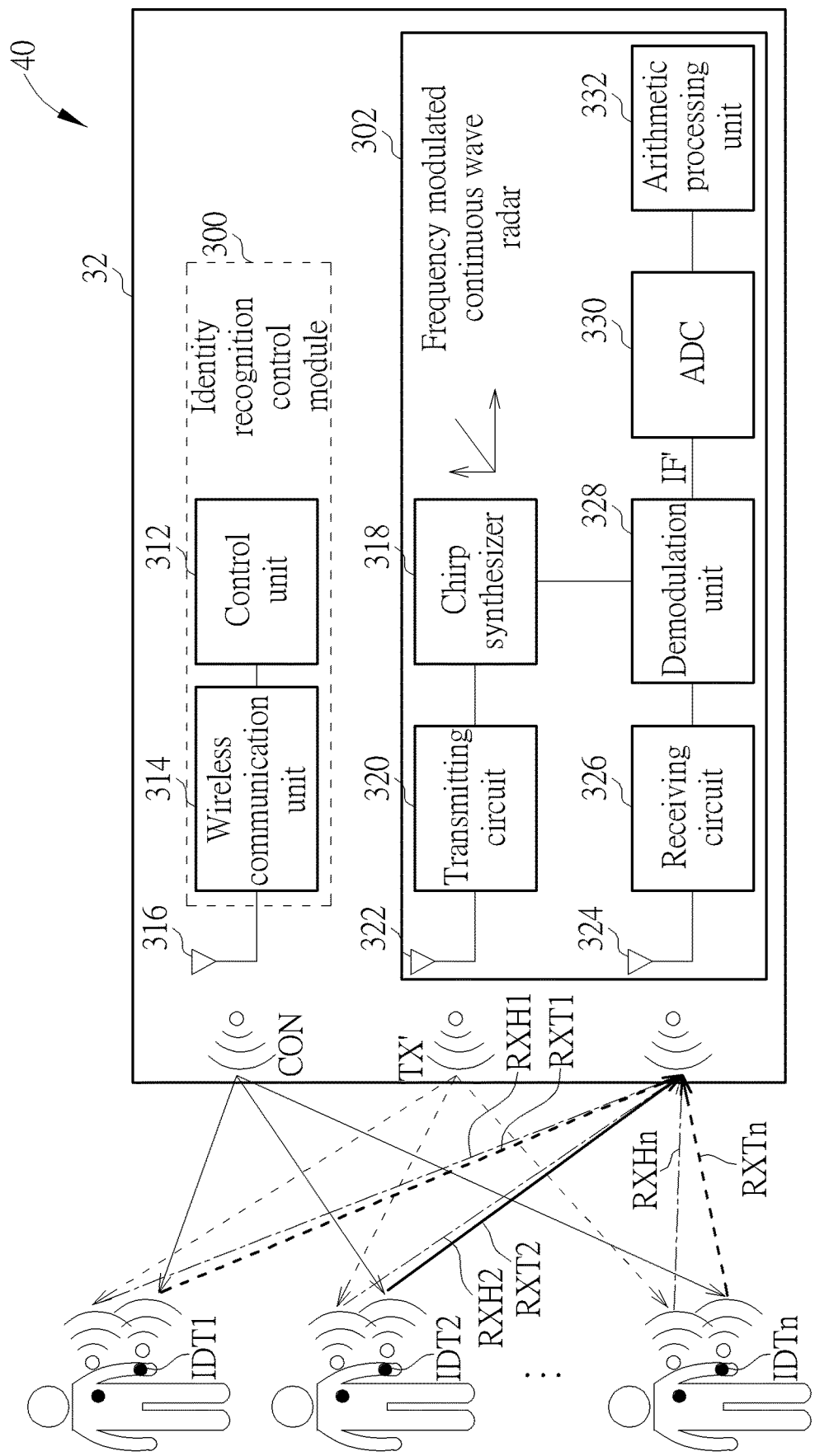
FIG. 4 is a schematic diagram of a frequency modulated continuous wave radar system according to another embodiment of the present invention.

For example, please refer to FIG. 4. FIG. 4 is a schematic diagram of a frequency modulated continuous wave radar system 40 according to an embodiment of the present invention. The frequency modulated continuous wave radar system 40 is similar to the frequency modulated continuous wave radar system 30, and hence the same numerals and notations denote components or signals of the same/similar functions in the following description for simplicity. The main difference between the frequency modulated continuous wave radar system 40 and the frequency modulated continuous wave radar system 30 is as follows: The frequency modulated continuous wave radar system 40 includes different identity tags IDT1 to IDTn (each having the same structure as the identity tag IDT) disposed adjacent to different test subjects (for example, on the hands of the test subjects). The identity recognition control module 300 may send a control signal CON, through wireless communication, to control/force a test identity tag IDT2 to be turned on (and corresponding to identity frequency) and the other identity tags (for example, the identity tags IDT1, and IDT3 to IDTn) to be turned off. In this case, after the frequency modulated continuous wave radar 302 emits a chirp signal TX', the frequency modulated continuous wave radar 302 may receive a tag reflection signal RXT2 of the identity tag IDT2 corresponding to the identity frequency and reflection signals RXH1 to RXHn of the test subjects in response to the chirp signal TX'. (Thick dashed lines indicate that tag reflection signals (for example, (tag) reflection signals RXT1, and RXT3 to RXTn) of the other identity tags (for example, the identity tags IDT1, and IDT3 to IDTn) do not correspond to the identity frequency and cannot be detected.) The frequency modulated continuous wave radar 302 may calculate and determine that the reflection signal RXH2 and the tag reflection signal RXT2 correspond to adjacent position information (for example, distance information and/or direction information), and obtain/have knowledge of the (test subject's) vital sign information (such as the breathing, and/or the heartbeat, and so on) corresponding to the test subject to be measured.

Please refer back to FIG. 3. Specifically, the control unit 312 is a control center of the frequency modulated continuous wave radar recognition device 32. The control unit 312 may perform wireless communication with the tag wireless communication unit 306 and the tag antenna 304 of the identity tag IDT by means of the wireless communication unit 314 and the control antenna 316. The control unit 312 may instruct the tag controller 308 of the identity tag IDT to turn on or off the tag reflector 310. The wireless communication may employ radio frequency identification RFID), WIFI, Bluetooth, ZigBee or other wireless communication technologies.

Next, the control unit 312 may control the frequency modulated continuous wave radar 302 to perform frequency modulated continuous wave detection. The operating principle of the frequency modulated continuous wave radar 302 is similar to that of the frequency modulated continuous wave radar 10. The chirp synthesizer 318 may generate a chirp signal TX'. Each chirp sub-signal in the chirp signal TX' may be the radio frequency oscillation signal (s) (having a start frequency of 77 gigahertz (GHz) and a stop frequency of 81 GHz, having a time period of 40 microseconds (µs), and having a modulation slope S of 100 MHz/µs) shown in FIG. 2A. However, each chirp sub-signal may comply with other signal specifications (such as a start frequency of 24 GHz). The transmitting circuit 320 includes a power amplifier (PA). The power amplifier of the transmitting circuit 320 can amplify the chirp signal TX', which is emitted through the transmitting antenna 322. The design of the transmitting antenna 322 is associated with the radio frequency being used and/or the effective field of view (FOV) being used.

In the case of the tag reflector 310 being turned on, when the identity tag IDT receives the chirp signal TX', the identity tag IDT may generate the tag reflection signal RXT corresponding to the identity frequency in response to the chirp signal TX'. Thus, the receiving antenna 324 may receive reflection signal(s) (including reflection signal(s) reflected off human body/bodies, the identity tag IDT, and/or stationary or moving object(s) in the environment, and so on) of the chirp signal TX' emitted by the transmitting antenna 322. Then, the receiving circuit 326 may perform front-end signal amplification and front-end filtering on the reflection signal(s). To design the receiving antenna 324, the frequency range of the radio frequency signal to be received and whether it is necessary to distinguish the direction of/to the test subject to be measured should be taken into account. If the direction of/to the test subject is to be distinguished, the design of multiple transmitting or receiving antennas should be considered.

In this case, although the main frequency of the different reflection signals is the same as the chirp signal TX', the different reflection signals have different characteristics. For example, the reflection intensities of different objects differ. (For instance, the intensity of the reflection signal reflected from a human body or metal is higher.) Moreover, the phase change of the reflection signal RXH formed by coupling the chest displacement caused by breathing and/or heartbeat corresponds to a specific physiological frequency. The tag reflection signal RXT corresponds to a specific identity frequency (such as the rotation frequency of a motor, the modulation frequency of a radar cross-section (RCS), or the vibration frequency of the vibrator of the tag reflector 310, and so on). The reflection signals propagating over different distances have different modulation frequency differences.

Furthermore, the demodulation unit 328 may demodulate (for example, couple) the reflection signal(s) (including the reflection signal RXH and the tag reflection signal RXT) received by the receiving circuit 326 with the (current) chirp signal TX' generated by the chirped synthesizer 318. The signal(s) after demodulation passes through a low pass filter to filter out radio frequency signal(s) (such as the chirp signal TX', the reflection signal RXH and the tag reflection signal RXT) so as to obtain/output an intermediate frequency signal IF'. The intermediate frequency signal IF' is converted from analog format into digital format by the analog-to-digital converter 330, which is convenient for the arithmetic processing unit 332 to process. Then, the arithmetic processing unit 332, by using various digital processing algorithms, removes noise(s), high-frequency signal(s), and/or inappropriate breathing harmonics so as to calculate the distance to be detected, the direction to be detected, and the identity information (such as the identity frequency) of the identity tag IDT to be detected, the human body distance to be detected, and/or the vital sign information (such as breathing, heartbeat, and so on) of the test subject to be detected. By comparison for the distance and/or the direction (made by the arithmetic processing unit 332 or the control unit 312), the control unit 312 then finds the identity information of the identity tag IDT and the vital sign information (such as human breathing, heartbeat, and so on) of the test subject at the same (or similar) distance (and/or in the same/adjacent direction), and hence determines the vital sign information (such as breathing, heartbeat, and so on) belongs to the test subject corresponding to the identity tag IDT. The arithmetic processing unit 332 and the control unit 312 may be integrated into one single processor.

Figure 5:
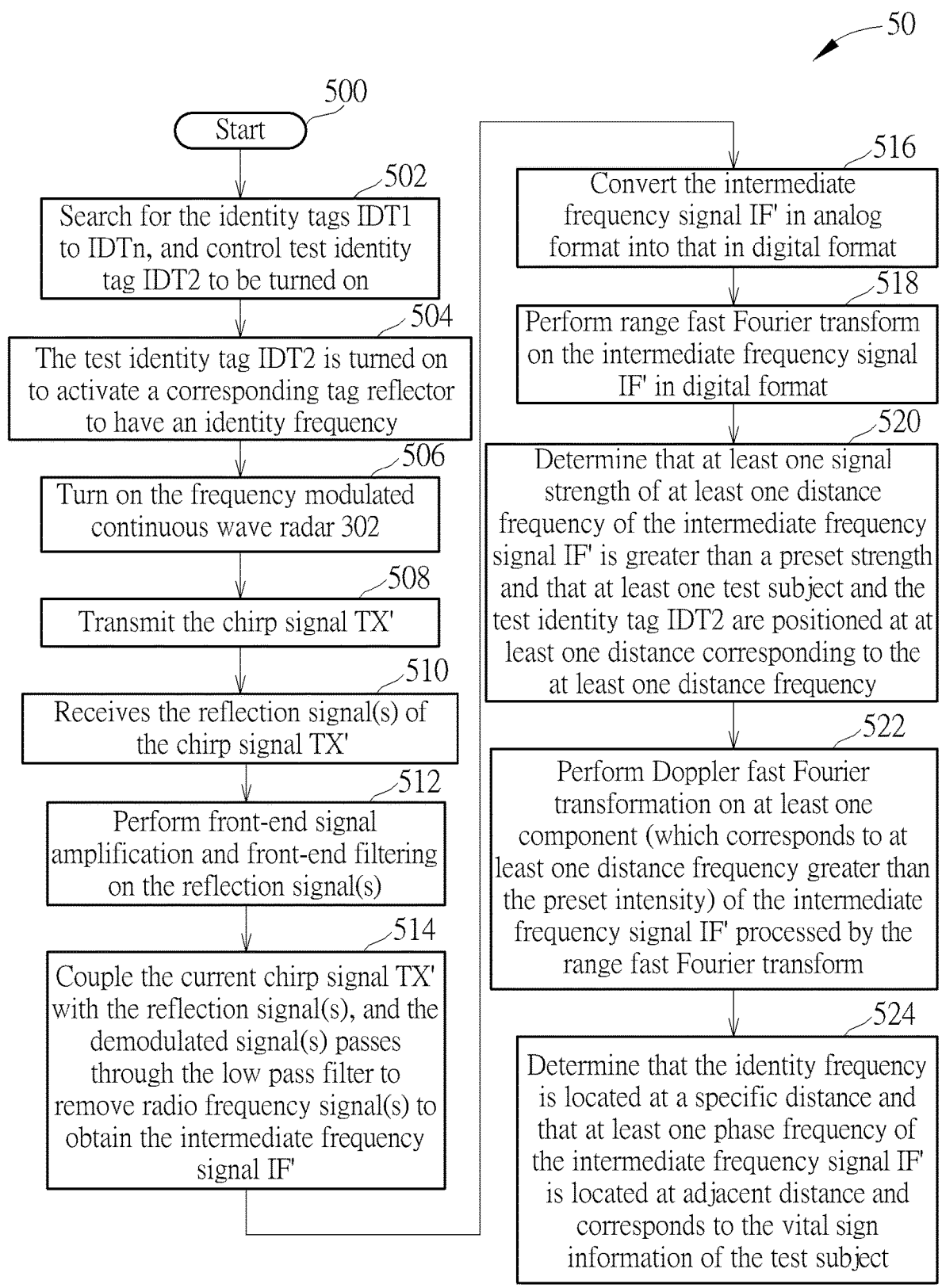
FIG. 5 is a schematic diagram of an identity and information detection process according to an embodiment of the present invention.

The operating principles of the frequency modulated continuous wave radar systems 30 and 40 may be summarized as an identity and information detection process 50. Specifically, please refer to FIG. 5. FIG. 5 is a schematic diagram of an identity and information detection process 50 according to an embodiment of the present invention. As shown in FIG. 5, the frequency modulated continuous wave radar recognition device 32 may search for the identity tags IDT1 to IDTn through the wireless communication unit 314, and control/force the test identity tag IDT2 to be turned on (step 502), such that the test identity tag IDT2 is turned on to activate a (corresponding) tag reflector to have an identity frequency (step 504). The identity frequency is a rotation frequency of a motor, a modulation frequency of a radar cross-section, or a vibration frequency of a vibrator of the corresponding tag reflector. Next, the frequency modulated continuous wave radar recognition device 32 activates the frequency modulated continuous wave radar 302 (step 506). The transmitting circuit 320 amplifies the chirp signal TX' generated by the chirp synthesizer 318 and transmits the chirp signal TX' through the transmitting antenna 322 (step 508). The chirp signal TX' includes N chirp sub-signals (which may be linearly increased from a start frequency of 77 GHz to a stop frequency of 81 GHz in each period/cycle as shown in FIG. 2A). The number of the chirp sub-signals is N.

Next, the receiving antenna 324 receives the reflection signal(s) of the chirp signal TX' (step 510). The receiving circuit 326 may perform front-end signal amplification and front-end filtering on the reflection signal(s) (step 512). The demodulation unit 328 couples the (current) chirp signal TX' with the reflection signal(s). The demodulated signal(s) passes through a low pass filter to remove radio frequency signal(s) so as to obtain/output an intermediate frequency signal IF' (step 514). The analog-to-digital converter 330 converts the intermediate frequency signal IF' in analog format into that in digital format (step 516).

Figure 6:
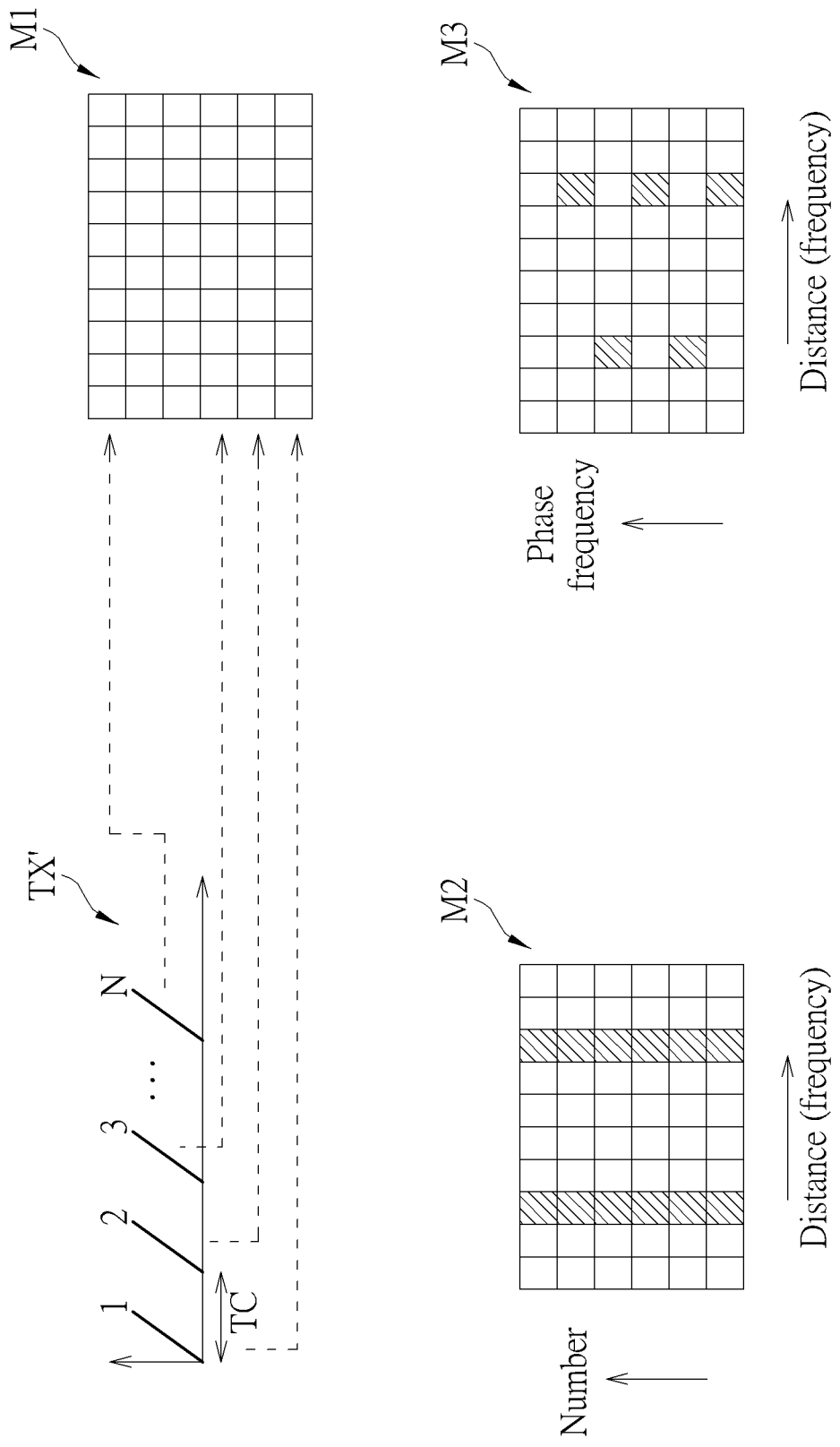
FIG. 6 is a schematic diagram of an operation of an arithmetic processing unit according to an embodiment of the present invention.

For example, please refer to FIG. 6. FIG. 6 is a schematic diagram of the operation of the arithmetic processing unit 332 according to an embodiment of the present invention. As shown in FIG. 6, the arithmetic processing unit 332 binds/converts each part/component (which is corresponding to each of the N chirp sub-signals of the chirp signal TX') of the intermediate frequency signal IF' in digital format as/into a matrix M1. Each horizontal part of the matrix M1 corresponds to sampling points sampled from a period TC of each of the N chirp sub-signals. The vertical part of the matrix M1 corresponds to the (different) chirp sub-signals numbered from 1 to N. (Different from FIG. 2A, the intensity of each chirp sub-signal may be zero at the end of each period TC to avoid the reflection signal of a (previous) chirp sub-signal from affecting the demodulation of another (following) chirp sub-signal.)

Next, the arithmetic processing unit 332 performs range fast Fourier transform (range FFT) on each row (namely, horizontal data) of the intermediate frequency signal IF' in digital format to create/obtain a matrix M2 (step 518). Each horizontal part of the matrix M2 corresponds to distance frequencies of each chirp sub-signal (and the corresponding distance(s) may be calculated according to FIG. 2B and related formula). The vertical part of the matrix M2 corresponds to the (different) chirp sub-signals numbered from 1 to N. In the distance frequency distribution figure being analyzed, if there is a distance frequency that exceeds a preset intensity, it means there is an object at the distance corresponding to the distance frequency. (For example, the reflection signal of a reflector being activated or a human body with higher reflection intensity may be designed to exceed the preset intensity.) The intensities of the distance frequencies represent the intensities of the reflection signals of object(s) at the corresponding distances. The distance frequency/frequencies can be converted into the corresponding distance(s) according to the slope of the N chirp sub-signals of the chirp signal TX'. Each frequency peak indicates that there is an object at that distance (namely, at a shaded array element in matrix M2). In other words, the arithmetic processing unit 332 may perform range fast Fourier transform on the intermediate frequency signal IF' to determine/find that/whether at least one signal strength of at least one distance frequency of the intermediate frequency signal IF' is greater than the preset strength and that/whether at least one test subject and the test identity tag IDT2 is (positioned at) at least one distance corresponding to the at least one distance frequency (from the frequency modulated continuous wave radar recognition device 32) (step 520).

Then, the arithmetic processing unit 332 performs (longitudinal) Doppler fast Fourier transform (Doppler-FFT) on the data at frequency peak(s) (that is, the shaded array element(s)) of the matrix M2 created/generated by the range fast Fourier transform to create/obtain a matrix M3 having phase change information of the intermediate frequency signal IF'. The phase change information represents phase frequency information (namely, information of the movement of an object, identity frequency such as the rotation frequency of a motor, or the modulation frequency of a radar cross-section, or the vibration frequency of a vibrator of a reflector, vital sign information (such as the breathing, and/or the heartbeat), and/or so on, which causes small displacement(s) hard to be detected in the frequency domain of the intermediate frequency signal IF' but able to be obtained/found by Doppler fast Fourier transform as intensity changes in different chirp sub-signals) of object(s) at a corresponding distance. The horizontal part of the matrix M3 corresponds to distance frequencies (representing distance) of each chirp sub-signal. The vertical part of the matrix M1 corresponds to phase frequency distribution of phase change(s) (that is, the magnitude(s) of phase frequency/frequencies of the phase change(s) at a certain distance).

In this case, the control unit 312 may determine whether each phase frequency peak of the vertical axis of the matrix M3 after Doppler fast Fourier transform is the identity frequency of the test identity tag IDT2. If so, it means that the corresponding distance is the distance where the test identity tag IDT2 is located. After finding/locating the distance position of the test identity tag IDT2, the control unit 312 then determines whether there are other phase frequency peak(s) at the adjacent distance(s) (vertical axis). If so, the control unit 312 analyzes/determines whether vital sign information, for instance, the frequency of the breathing, and/or the heartbeat, is included. If so, it means that the vital sign information (such as the breathing, and/or the heartbeat, and so on) is the information possessed by the test subject with the test identity tag IDT2. In this way, according to information processed by the frequency modulated continuous wave radar 302, the control unit 312 can identify/link object (namely, the test identity tag IDT2) with the phase frequency (such as the vibration frequency, the rotation frequency of the motor or the modulation frequency of the radar cross-section) of a specific value. Moreover, the control unit 312 may use the vital sign information (such as the breathing, and/or the heartbeat) of adjacent object(s) as the vital sign information of the test subject of the test identity tag IDT2, and use the distance position as the distance position of the test subject.

For example, the identity frequency of the test identity tag IDT2 may generally be set higher than the frequency/frequencies of the vital sign(s) (such as the breathing, and/or the heartbeat) to reduce misjudgment during processing. (For example, the vibration frequency is set to 1 kilohertz (KHz). Alternatively, the modulation frequency of the radar cross-section is set to 5 KHz.) The control unit 312 may determine that/whether the identity frequency of the test identity tag IDT2 is at a specific frequency (distance) on the right side of the matrix M3 (such as the shaded array element(s) on the top right), and then determine that/whether the phase frequency peak(s) at lower adjacent position(s) is the frequency/frequencies of the vital sign(s) (such as the breathing, and/or the heartbeat) of the test subject. In other words, the arithmetic processing unit 332 performs Doppler fast Fourier transformation on at least one component (that is, the shaded area/array element(s) of the matrix M2) (which corresponds to at least one distance frequency greater than the preset intensity) of the intermediate frequency signal IF' processed by the range fast Fourier transform (Step 522), such that the control unit 312 determines that the identity frequency is located at a specific distance and that at least one phase frequency (which is located at adjacent distance and thus has adjacent position information) of the intermediate frequency signal IF' corresponds to the vital sign information of the test subject (step 524).

The aforementioned embodiment(s) focus on that the tag reflector of a specific identity tag is turned on to have an identity frequency so as to obtain/have knowledge of the vital sign information of the test subject adjacent to specific identity tag(s) and intended to be measured. The present invention is not limited thereto, and those skilled in the art may readily make alterations and modifications. For example, in the aforementioned embodiment (s), the (current) chirp signal TX' is coupled with the reflection signal to obtain/derive the intermediate frequency signal IF'. Then, the distance frequency (whose signal strength is greater than a preset strength) in the intermediate frequency signal IF' is determined to be/correspond to the distance from/at which the human body or the reflector being turned on is located. Then, at least one phase frequency (which has/corresponds to an adjacent distance with the identity frequency) is determined to have adjacent position information and correspond to the vital sign information of the test subject. In other embodiments, in addition to having/corresponding to an adjacent distance, an adjacent direction would also be considered to determine to have adjacent position information.

Figure 7:
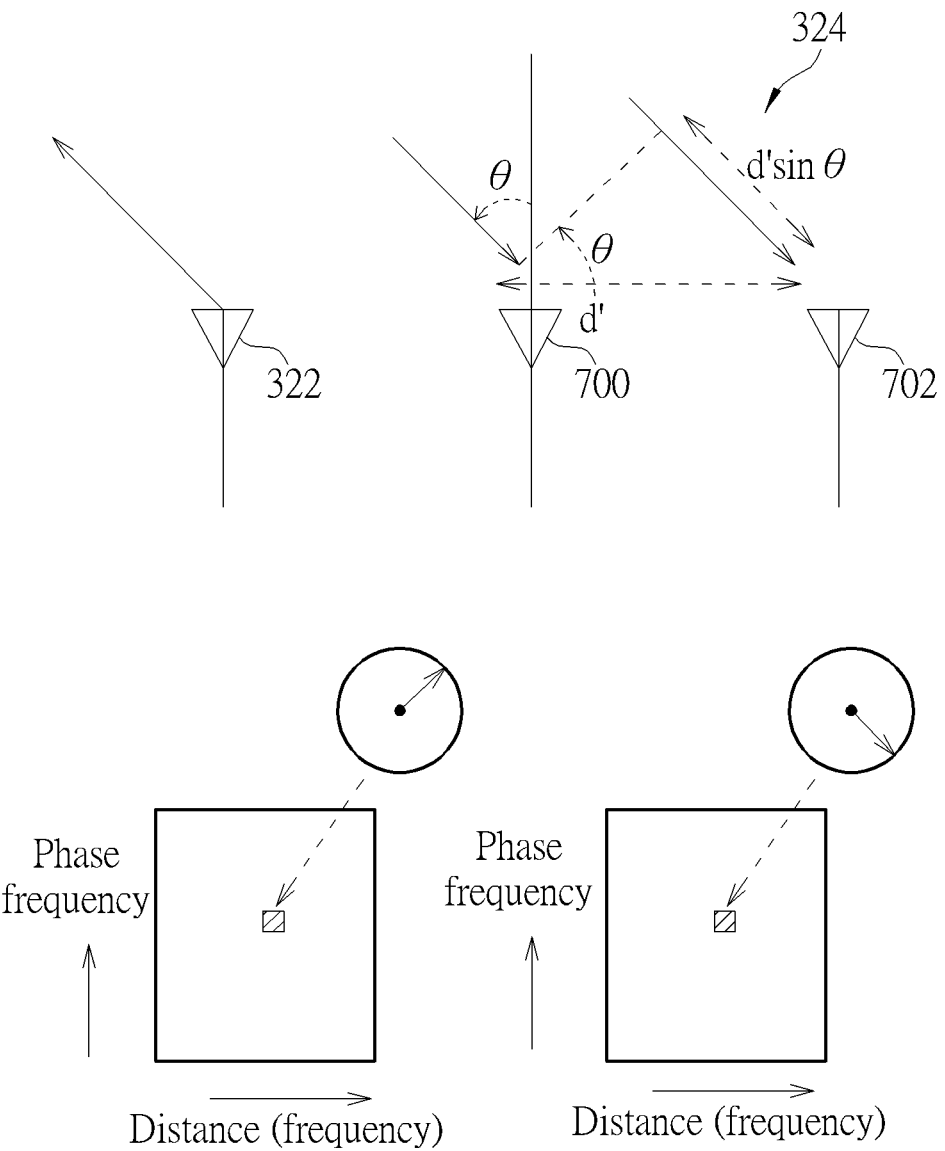
FIG. 7 is a schematic diagram of an angle of arrival of the reflection signal of the chirp signal according to an embodiment of the present invention.

Please refer to FIG. 7. FIG. 7 is a schematic diagram of an angle of arrival (AOA) of the reflection signal of the chirp signal TX' according to an embodiment of the present invention. As shown in FIG. 7, the receiving antenna 324 may include receiving sub-antennas 700 and 702. The receiving sub-antennas 700 and 702 are separated by a distance d'. The receiving sub-antennas 700 and 702 are configured to receive the reflection signals RXH1 to RXHn and the tag reflection signal RXT so as to determine multiple corresponding angles of arrival. Specifically, since the distance between the test subject to be measured and the receiving sub-antenna 700 is different from the distance between the test subject to be measured and the receiving sub-antenna 702, the timing for the reflection signal of the chirp signal TX' emitted by the transmitting antenna 322 to reach the receiving sub-antenna 700 may differ from the timing for the reflection signal of the chirp signal TX' emitted by the transmitting antenna 322 to reach the receiving sub-antenna 702. Therefore, the phases of the reflection signals vary. The phase difference may be expressed as follows:

$$w_2 = \frac{2\pi d' \sin\theta}{\lambda} \rightarrow \theta = \sin^{-1}\left(\frac{\lambda w_2}{2\pi d'}\right)$$

where θ represents the angle of arrival of the reflection signal. Therefore, according to the phase difference of the reflection signals received by the receiving sub-antennas 700 and 702, the direction of the test subject to be measured may be detected. Besides, only when it has an adjacent distance and an adjacent direction can it be determined to have similar position information.

For example, as shown at lower part of FIG. 7, the phase frequency of the intermediate frequency signal IF' obtained after the range fast Fourier transform and the Doppler fast Fourier transform have the information of the respective angles of arrival respectively. Therefore, after at least one phase frequency and the identity frequency are determined to have adjacent distance(s), it is necessary to determine that/whether the at least one phase frequency and the identity frequency have adjacent direction(s) in order to determine that/whether the at least one phase frequency and the identity frequency have similar position information and correspond to the vital sign information of the test subject. (That is, the adjacent position information includes the adjacent distance(s) and the adjacent direction(s).) In addition, in the embodiment shown in FIG. 7, two receiving sub-antennas 700 and 702 are used to determine the direction of the test subject under test. However, in other embodiments, more receiving sub-antennas may be used to increase the resolution so as to accurately detect/measure the direction of/from the location of multiple objects (such as test subjects).

In addition, in the aforementioned embodiment (s), the identity frequency may be the rotation frequency of a motor, the modulation frequency of a radar cross-section, or the vibration frequency of a vibrator of the tag reflector 310 being turned on. The implementation of the tag reflector 310 is however not limited, as long as the tag reflector 310 being turned on can make the reflection signal have a phase change corresponding to the identity frequency after activation. In short, the tag reflector 310 may include a vibrator. The vibrator can make specific vibrations and reflect the chirp signal TX'; alternatively, the vibrator can backscatter to respond to and modulate the chirp signal TX' (for example, to change the radar cross-section with the modulation frequency).

In an embodiment for the tag reflector 310, to generate vibration, a speaker (vibrating) diaphragm/membrane may be used and a specific vibration signal (which, for instance, has a specific vibration frequency to serve as the identity frequency) may be provided; alternatively, a mobile phone vibrator may be used to generate vibration. In addition, to effectively increase the intensity of the reflection signal of the chirp signal TX', the speaker membrane maybe coated with a metal film; alternatively, the structure of the speaker membrane may be designed similar to that of a corner reflector (or a collection/assembly of miniaturized corner reflectors) to enhance the intensity of the reflection signal of the chirp signal TX'.

Specifically, the corner reflector may be of a right-angled pyramid structure or a dihedral corner reflector. With this geometric structure, an incident signal can be reflected back and (the reflection is) parallel to the incident signal, thereby ensuring a relatively high radar cross-section to be possessed. In addition, if only one single corner reflector is designed for the speaker membrane, a problem of thickness (for example, a problem of being too thick) would arise. Therefore, a collection of multiple miniaturized corner reflectors may be designed for the speaker membrane. By reducing the size, the overall structure can become thinner while similar radar cross-section(s) maintains. In the case that the speaker membrane or the mobile phone vibrator has a corner reflector or a collection of miniaturized corner reflectors, when a selected vibration frequency (namely, the identity frequency) is given to vibrate the speaker membrane or the mobile phone vibrator, the reflection signal has more obvious change(s) corresponding to the identity frequency such that the distance and the identity frequency may be analyzed/found. The aforementioned embodiments mainly use the speaker membrane or the mobile phone vibrator able to vibrate at the vibration frequency, and use the structure of a corner reflector as a reflecting surface. Other features of a speaker are well known to those skilled in the art, and are not detailed redundantly for brevity.

Figure 8:
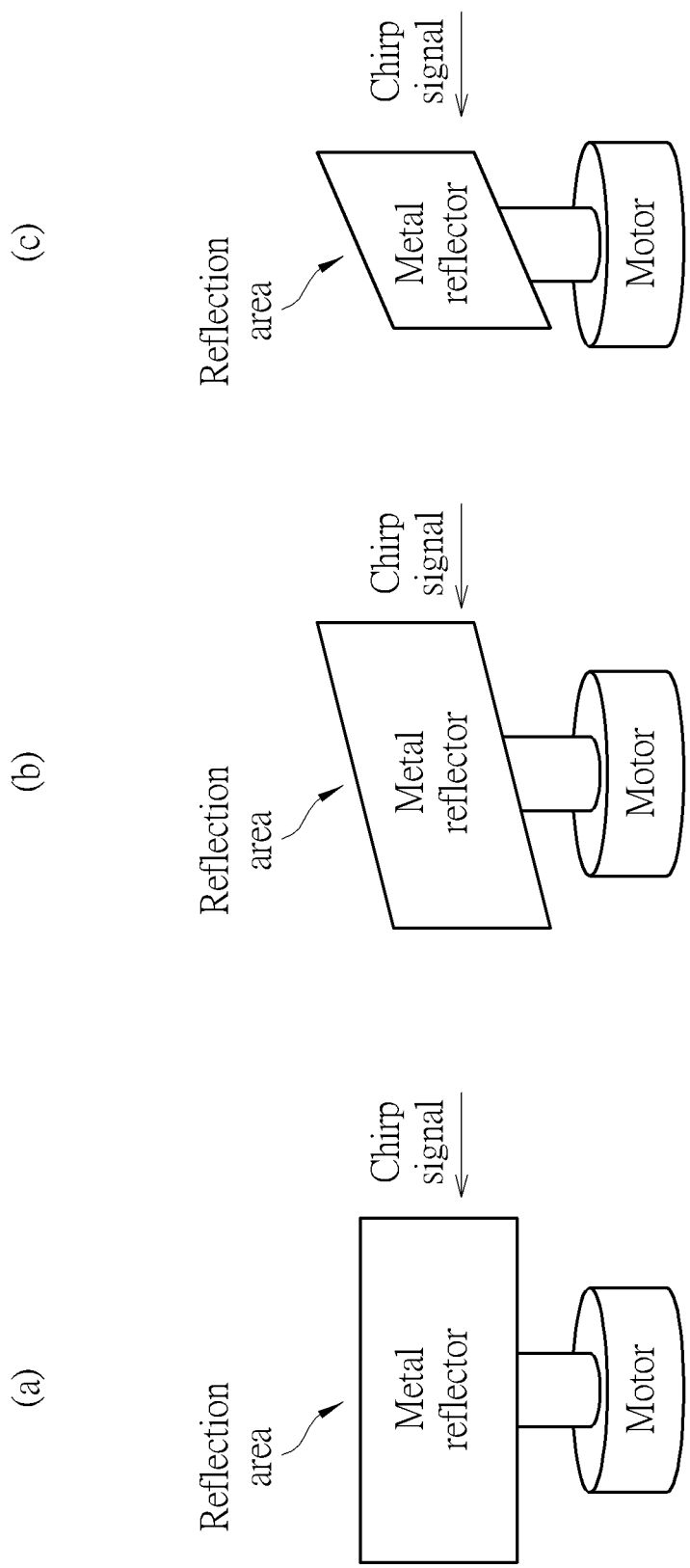
FIG. 8 is a schematic diagram of how a motor controls a metal reflector to rotate according to an embodiment of the present invention.

Furthermore, in another embodiment of the tag reflector 310, as shown in FIG. 8, a motor may be used to control a metal reflector to rotate at a rotational frequency (namely, the identity frequency), such that the reflection area (radar cross-section) of metal reflector with respect to (relative to) the chirp signal TX' being modulated changes according to the rotation frequency.

In addition, in another embodiment of the tag reflector 310, backscatter transponder(s) of frequency selective surface(s) (FSS) being actively controlled may be used. The frequency selective surface (s) may include dipole (s) equipped with switching PIN diode (s). The transponder controls the bias voltage of the diode to modulate the change of the radar cross-section of the frequency selective surface so as to modulate the backscatter response of the tag to the frequency modulated continuous wave radar 302. By appropriately selecting the design of a frequency selective surface resonator and the PIN diode, the scanning frequency of the chirp signal TX' of the frequency modulated continuous wave radar 302 can be covered. For example, the frequency selective surface has a longer antenna length when the PIN diode is turned on. The antenna length may be appropriately designed to resonate with the chirp signal TX' so as to ensure a stronger reflection signal. Therefore, the bias voltage of the diode may be controlled to modulate/adjust the radar cross-section of the frequency selective surface according to the modulation frequency, such that the reflection signal has a strength change (namely, being strong or weak) corresponding to the modulation frequency (the identity frequency).

In addition, in another embodiment of the tag reflector 310, a resonator of an integrated circuit being actively controlled may be used. After the integrated circuit receives the chirp signal TX' through the antenna, a resonance signal is generated by a match network and a resonator. Then, the control signal determines whether to transmit the resonance signal serving as a reflection signal according to the modulation frequency. That is, the resonance signal generated by the resonator is modulated according to the modulation frequency, such that the reflection signal is forced to have a strength change (namely, being strong or weak) corresponding to the modulation frequency (the identity frequency).

In the aforementioned embodiment, after the tag reflector 310 is turned on to have the identity frequency, it is noteworthy that the tag reflection signal RXT may not only have a phase change corresponding to the identity frequency.

The frequency of the tag reflection signal RXT may be the frequency corresponding to the chirp signal TX' plus or minus the identity frequency because of the frequency coupling of the identity frequency and the chirp signal TX'. As a result, the observed/measured distance frequency of the test identity tag IDT is equal to the actual distance frequency plus or minus the identity frequency. In this case, after the range fast Fourier transform is performed, two distance frequencies corresponding to the identity frequency of the tested identity tag IDT may be found first. The two distance frequencies are added and averaged to obtain/calculate the actual distance frequency. The distance frequency is subtracted and averaged to obtain/calculate the identity frequency.

In addition, in the aforementioned embodiment, the identity tag is placed next to the test subject to detect/measure the vital sign information of the test subject. However, in other embodiments, the test subject may be a non-human object/entity, and other information of the test subject is to be detected. For example, the present invention may be applied to detect/locate the location of a specific object. Specifically, the frequency modulated continuous wave radar can detect/measure the distance and the speed of an object without knowledge of what the object is. If the identity tag is disposed on an object (such as a car), when the car is moving (or stationary), the frequency modulated continuous wave radar 302 can determine whether/that the object being measured is (identified as) the car with the identity tag by determining whether/that the (measured) distance and the (measured) speed of the object is the same as (or similar to) the (measured) distance and the (measured) speed of the identity tag.

Furthermore, the tag controller 308, the control unit 312 and the arithmetic processing unit 332 may be a processor, such as a microprocessor or an application-specific integrated circuit (ASIC). The identity tag IDT and the frequency modulated continuous wave radar recognition device 32 may include a storage unit respectively. The storage unit may be any data storage device configured to store a program code. The program code may be read and executed by the processor to perform the above-mentioned related operations. The storage unit may be a subscriber identity module (SIM), a read-only memory (ROM), a random-access memory (RAM), a compact disc read-only memory (CD-ROM), a magnetic tapes, a floppy disk, or an optical data storage device, and so on, but are not limited thereto.

In summary, the present invention may turn on a tag reflector of a specific identity tag to have an identity frequency, so as to obtain information about a test subject adjacent to the specific identity tag and intended to be measured.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A frequency modulated continuous wave radar system, comprising:
   at least one identity tag, respectively disposed next to at least one test subject; and
   a frequency modulated continuous wave radar identity recognition device, comprising:
   an identity recognition control module, for transmitting a control signal to control a test identity tag of the at least one identity tag to be turned on and to make the test identity tag generate a specific tag reflection signal corresponding to an identity frequency in response to a chirp signal; and a frequency modulated continuous wave radar, for transmitting the chirp signal, wherein the frequency modulated continuous wave radar receives at least one reflection signal of the at least one test subject and the specific tag reflection signal in response to the chirp signal, such that the frequency modulated continuous wave radar calculates and determines that the specific tag reflection signal and a specific reflection signal of the at least one reflection signal correspond to an adjacent position information;

wherein the specific reflection signal corresponds to a test subject information, wherein the frequency modulated continuous wave radar performs a range fast Fourier transform (FFT) on an intermediate frequency signal so as to determine at least one signal intensity of at least one distance frequency of the intermediate frequency signal is greater than a preset intensity and the at least one test subject and the test identity tag are located at at least one distance corresponding to the at least one distance frequency, wherein the frequency modulated continuous wave radar performs a Doppler fast Fourier transform on at least one component corresponding to the at least one distance frequency greater than the preset intensity of the intermediate frequency signal being performed by the range fast Fourier transform, so as to determine the identity frequency is generated at an adjacent distance of the adjacent position information and at least one phase frequency of the intermediate frequency signal located at the adjacent distance is corresponding to the test subject information.

2. The frequency modulated continuous wave radar system of claim 1, wherein the test identity tag is turned on to activate a corresponding reflector to have the identity frequency, and the identity frequency is a rotation frequency of a motor, a modulation frequency, or a vibration frequency of the corresponding reflector.

3. The frequency modulated continuous wave radar system of claim 1, wherein the chirp signal comprises a plurality of chirp sub-signals, and each of the plurality of chirp sub-signals linearly increases from a start frequency to a stop frequency in each cycle.

4. The frequency modulated continuous wave radar system of claim 1, wherein the frequency modulated continuous wave radar performs demodulation and low-pass filtering on the at least one reflection signal and the specific tag reflection signal with the current chirp signal, to generate the intermediate frequency signal.

5. The frequency modulated continuous wave radar system of claim 1, wherein the frequency modulated continuous wave radar comprises a plurality of receiving sub-antenna configured for receiving the at least one reflection signal and the specific tag reflection signal to determine a plurality of corresponding angles of arrival, and the adjacent position information comprises the adjacent distance and an adjacent direction.

6. The frequency modulated continuous wave radar system of claim 2, wherein a speaker membrane or a mobile phone vibrator in the corresponding reflector vibrates at the vibration frequency, and the speaker membrane or the mobile phone vibrator has a structure of a corner reflector or a miniaturized corner reflector assembly.

7. The frequency modulated continuous wave radar system of claim 2, wherein the motor controls a metal reflector to rotate at the rotation frequency such that a reflection area of the metal reflector with respect to the chirp signal varies according to the rotation frequency.

8. The frequency modulated continuous wave radar system of claim 2, wherein a radar cross-section of a frequency selective surface of the corresponding reflector is modulated according to the modulation frequency, or a resonance signal generated by a resonator of the corresponding reflector is modulated according to the modulation frequency.

9. An identity and information detection method, for a frequency modulated continuous wave radar system comprising at least one identity tag respectively disposed next to at least one test subject, wherein the method comprises:

transmitting a control signal to control a test identity tag of the at least one identity tag to be turned on;

transmitting, by a frequency modulated continuous wave radar, a chirp signal;

generating, by the test identity tag, a specific tag reflection signal corresponding to an identity frequency in response to the chirp signal; and receiving, by the frequency modulated continuous wave radar, at least one reflection signal of the at least one test subject and the specific tag reflection signal in response to the chirp signal, such that the frequency modulated continuous wave radar calculates and determines that the specific tag reflection signal and a specific reflection signal of the at least one reflection signal correspond to an adjacent position information;

wherein the specific reflection signal corresponds to a test subject information, wherein the frequency modulated continuous wave radar performs a range fast Fourier transform (FFT) on an intermediate frequency signal so as to determine at least one signal intensity of at least one distance frequency of the intermediate frequency signal is greater than a preset intensity and the at least one test subject and the test identity tag are located at at least one distance corresponding to the at least one distance frequency, wherein the frequency modulated continuous wave radar performs a Doppler fast Fourier transform on at least one component corresponding to the at least one distance frequency greater than the preset intensity of the intermediate frequency signal being performed by the range fast Fourier transform, so as to determine the identity frequency is generated at an adjacent distance of the adjacent position information and at least one phase frequency of the intermediate frequency signal located at the adjacent distance is corresponding to the test subject information.

10. The identity and information detection method of claim 9, further comprising:

turning on the test identity tag to activate a corresponding reflector to have the identity frequency, wherein the identity frequency is a rotation frequency of a motor, a modulation frequency, or a vibration frequency of the corresponding reflector.

11. The identity and information detection method of claim 9, wherein the chirp signal comprises a plurality of chirp sub-signals, and each of the plurality of chirp sub-signals linearly increases from a start frequency to a stop frequency in each cycle.

12. The identity and information detection method of claim 9, wherein the frequency modulated continuous wave radar performs demodulation and low-pass filtering on the at least one reflection signal and the specific tag reflection signal with the current chirp signal, to generate the intermediate frequency signal.

13. The identity and information detection method of claim 9, wherein the frequency modulated continuous wave radar comprises a plurality of receive sub-antenna configured for receiving the at least one reflection signal and the specific tag reflection signal to determine a plurality of corresponding angles of arrival, and the adjacent position information comprises the adjacent distance and an adjacent direction.

14. The identity and information detection method of claim 10, wherein a speaker membrane or a mobile phone vibrator in the corresponding reflector vibrates at the vibration frequency, and the speaker membrane or the mobile phone vibrator has a structure of a corner reflector or a miniaturized corner reflector assembly.

15. The identity and information detection method of claim 10, wherein the motor controls a metal reflector to rotate at the rotation frequency such that a reflection area of the metal reflector with respect to the chirp signal varies according to the rotation frequency.

16. The identity and information detection method of claim 10, wherein a radar cross-section of a frequency selective surface of the corresponding reflector is modulated according to the modulation frequency, or a resonance signal generated by a resonator of the corresponding reflector is modulated according to the modulation frequency.

* * * * *